(12) United States Patent
Baldwin et al.

(10) Patent No.: US 6,743,233 B1
(45) Date of Patent: Jun. 1, 2004

(54) MEDICAL SCREW AND METHOD OF INSTALLATION

(75) Inventors: Jeffrey P. Baldwin, Phoenix, AZ (US); Laird Hatch, Cave Creek, AZ (US)

(73) Assignee: Orthopaedic Biosystems, Ltd., Inc., Memphis, TN (US)

( * ) Notice: Subject to any disclaimer, the term of this patent is extended or adjusted under 35 U.S.C. 154(b) by 102 days.

(21) Appl. No.: 09/630,401

(22) Filed: Aug. 2, 2000

(51) Int. Cl.⁷ .............................................. A61B 17/56
(52) U.S. Cl. ........................................ 606/73; 606/232
(58) Field of Search ............................ 606/65, 66, 73, 606/232

(56) References Cited

U.S. PATENT DOCUMENTS

| | | |
|---|---|---|
| 1,105,105 A | 7/1914 | Sherman |
| 1,247,621 A | 11/1917 | Bennett |
| 1,410,088 A | 3/1922 | White |
| 1,809,758 A | 6/1931 | Rosenberg |
| 2,100,570 A | 11/1937 | Saleh |
| 2,143,086 A | 1/1939 | Pleister |
| 2,242,003 A | 5/1941 | Lorenzo |
| 2,263,137 A | 11/1941 | Oestereicher |
| 2,267,925 A * | 12/1941 | Johnson ........................ 606/73 |
| 2,329,398 A | 9/1943 | Duffy |
| 2,381,050 A | 8/1945 | Hardinge |
| 2,397,545 A | 4/1946 | Hardinge |
| 2,414,882 A | 1/1947 | Longfellow |
| 2,570,465 A | 10/1951 | Lundholm |
| 2,685,877 A | 8/1954 | Dobelle |
| 3,003,155 A | 10/1961 | Mielzynski et al. |
| 3,207,023 A | 9/1965 | Khohl |
| 3,227,031 A | 1/1966 | Williams |
| 3,233,500 A | 2/1966 | De Vellier |
| 3,273,442 A | 9/1966 | Launay |
| 3,289,290 A | 12/1966 | Sandor |
| 3,312,139 A | 4/1967 | DiCristina |
| 3,316,796 A | 5/1967 | Young |
| 3,405,595 A | 10/1968 | Peterson |
| 3,463,209 A | 8/1969 | Podolsky |

(List continued on next page.)

FOREIGN PATENT DOCUMENTS

| | | |
|---|---|---|
| EP | 0232049 A1 | 8/1987 |
| EP | 0260970 A2 | 3/1988 |
| EP | 0270704A1 B1 | 6/1988 |
| EP | 0340159 A1 | 11/1989 |
| EP | 0374088 A1 | 6/1990 |

(List continued on next page.)

OTHER PUBLICATIONS

STATAK™ Soft Tissue Attachment Device, Zimmer brochure.

Adelman, "Arthroscopic Bankart suturing yields better external rotation," Orthopedics Today, Feb. 1989.

Goble, E. M., "Fluoroarthroscopic allograft anterior cruciate reconstruction," Techniques in Orthopedics, vol. 2, Issue 4 (1988).

"Orthopedic Catalog," p. 145, Richards Manufacturing Co., Inc., Memphis, TN (1979).

(List continued on next page.)

*Primary Examiner*—Todd E. Manahan
(74) *Attorney, Agent, or Firm*—Fish & Richardson P.C.

(57) ABSTRACT

A medical screw includes a shaft having a threaded portion and a distal guiding tip for introducing the screw into a pre-drilled implantation site. The threaded portion of the medical screw has a first series of helical threads having a first diameter and a second series of helical threads interleaved with the first series of helical thread and having a second diameter, where the first diameter is different than the second diameter. In addition, the medical screw may have a counter-rotation channel configured to receive bone growth.

4 Claims, 9 Drawing Sheets

U.S. PATENT DOCUMENTS

| | | | | |
|---|---|---|---|---|
| 3,466,748 A | * | 9/1969 | Christensen | ................ 606/73 |
| 3,499,222 A | | 3/1970 | Linkow et al. | |
| 3,566,739 A | | 3/1971 | Lebar | |
| 3,708,883 A | | 1/1973 | Flander | |
| 3,832,931 A | | 9/1974 | Talan | |
| 3,861,269 A | | 1/1975 | Laverty | |
| 3,953,896 A | | 5/1976 | Treace | |
| 4,013,071 A | | 3/1977 | Rosenberg | |
| 4,175,555 A | | 11/1979 | Herbert | |
| 4,275,717 A | | 6/1981 | Bolesky | |
| 4,325,153 A | | 4/1982 | Finnegan | |
| 4,408,938 A | | 10/1983 | Maguire | |
| 4,454,875 A | | 6/1984 | Pratt et al. | |
| 4,463,753 A | | 8/1984 | Gustilo | |
| 4,484,570 A | | 11/1984 | Sutter et al. | |
| 4,532,926 A | | 8/1985 | O'Holla | |
| 4,537,185 A | | 8/1985 | Stednitz | |
| 4,573,844 A | | 3/1986 | Smith | |
| 4,590,928 A | | 5/1986 | Hunt et al. | |
| 4,632,100 A | | 12/1986 | Somers et al. | |
| 4,636,121 A | | 1/1987 | Miller | |
| 4,655,661 A | | 4/1987 | Brandt | |
| 4,708,132 A | | 11/1987 | Silvestrini | |
| 4,711,232 A | | 12/1987 | Fischer et al. | |
| 4,711,234 A | | 12/1987 | Vives et al. | |
| 4,716,893 A | | 1/1988 | Fischer et al. | |
| 4,744,793 A | | 5/1988 | Parr et al. | |
| 4,776,328 A | | 10/1988 | Frey et al. | |
| 4,834,752 A | | 5/1989 | Van Kampen | |
| 4,870,957 A | | 10/1989 | Goble et al. | |
| 4,871,289 A | | 10/1989 | Choiniere | |
| 4,884,572 A | | 12/1989 | Bays et al. | |
| 4,895,148 A | | 1/1990 | Bays et al. | |
| 4,924,865 A | | 5/1990 | Bays et al. | |
| 4,940,467 A | | 7/1990 | Tronzo | |
| 4,950,270 A | | 8/1990 | Bowman et al. | |
| 4,976,715 A | | 12/1990 | Bays et al. | |
| 4,988,351 A | | 1/1991 | Paulos et al. | |
| 5,013,316 A | | 5/1991 | Goble et al. | |
| 5,061,136 A | | 10/1991 | Dixon et al. | |
| 5,061,187 A | | 10/1991 | Jerath | |
| 5,067,956 A | | 11/1991 | Buford, III et al. | |
| 5,084,050 A | | 1/1992 | Draenert | |
| 5,087,201 A | * | 2/1992 | Mondani et al. | ............ 433/174 |
| 5,098,435 A | | 3/1992 | Stednitz et al. | |
| 5,100,417 A | | 3/1992 | Cerier et al. | |
| 5,102,421 A | | 4/1992 | Anspach, Jr. | |
| 5,108,431 A | | 4/1992 | Mansat et al. | |
| 5,116,337 A | | 5/1992 | Johnson | |
| 5,129,906 A | | 7/1992 | Ross et al. | |
| 5,139,499 A | | 8/1992 | Small et al. | |
| 5,156,616 A | | 10/1992 | Meadows et al. | |
| D331,626 S | | 12/1992 | Hayhurst et al. | |
| 5,209,753 A | | 5/1993 | Biedermann et al. | |
| 5,211,647 A | | 5/1993 | Schmieding | |
| RE34,293 E | | 6/1993 | Goble et al. | |
| 5,224,946 A | | 7/1993 | Hayhurst et al. | |
| 5,234,430 A | | 8/1993 | Huebner | |
| 5,236,445 A | | 8/1993 | Hayhurst et al. | |
| 5,246,441 A | | 9/1993 | Ross et al. | |
| 5,258,016 A | | 11/1993 | DiPoto et al. | |
| 5,268,001 A | | 12/1993 | Nicholson et al. | |
| 5,273,545 A | | 12/1993 | Hunt et al. | |
| 5,294,227 A | | 3/1994 | Forster et al. | |
| 5,336,225 A | | 8/1994 | Zang | |
| 5,336,240 A | | 8/1994 | Metzler et al. | |
| 5,354,299 A | | 10/1994 | Coleman | |
| 5,364,400 A | | 11/1994 | Rego, Jr. et al. | |
| 5,370,662 A | | 12/1994 | Stone et al. | |
| RE34,871 E | | 3/1995 | McGuire et al. | |
| 5,397,356 A | | 3/1995 | Goble et al. | |
| 5,411,506 A | | 5/1995 | Goble et al. | |
| 5,411,523 A | | 5/1995 | Goble | |
| 5,417,712 A | | 5/1995 | Whittaker et al. | |
| RE34,969 E | | 6/1995 | Dixon et al. | |
| 5,423,819 A | | 6/1995 | Small et al. | |
| 5,425,733 A | | 6/1995 | Schmieding | |
| 5,425,767 A | | 6/1995 | Steininger et al. | |
| 5,443,482 A | | 8/1995 | Stone et al. | |
| 5,443,509 A | | 8/1995 | Boucher et al. | |
| 5,454,811 A | | 10/1995 | Huebner | |
| 5,456,685 A | | 10/1995 | Huebner | |
| 5,464,427 A | | 11/1995 | Curtis et al. | |
| 5,466,243 A | | 11/1995 | Schmieding et al. | |
| 5,470,334 A | | 11/1995 | Ross et al. | |
| 5,480,403 A | | 1/1996 | Lee et al. | |
| 5,486,197 A | | 1/1996 | Le et al. | |
| 5,489,210 A | | 2/1996 | Hanosh | |
| 5,492,442 A | * | 2/1996 | Lasner | ................... 606/73 |
| 5,496,326 A | | 3/1996 | Johnson | |
| 5,522,843 A | | 6/1996 | Zang | |
| 5,522,845 A | | 6/1996 | Wenstrom, Jr. | |
| 5,545,180 A | | 8/1996 | Le et al. | |
| 5,562,672 A | | 10/1996 | Huebner et al. | |
| 5,571,104 A | | 11/1996 | Li | |
| 5,573,548 A | | 11/1996 | Nazre et al. | |
| 5,578,057 A | | 11/1996 | Wenstrom, Jr. | |
| 5,591,207 A | | 1/1997 | Coleman | |
| 5,607,432 A | | 3/1997 | Fucci | |
| 5,626,613 A | | 5/1997 | Schmieding | |
| 5,628,766 A | * | 5/1997 | Johnson | ................ 606/232 |
| 5,632,748 A | | 5/1997 | Beck, Jr. et al. | |
| 5,643,321 A | | 7/1997 | McDevitt | |
| 5,649,963 A | | 7/1997 | McDevitt | |
| 5,662,683 A | | 9/1997 | Kay | |
| D385,352 S | | 10/1997 | Bales et al. | |
| 5,683,401 A | | 11/1997 | Schmieding et al. | |
| 5,690,676 A | | 11/1997 | DiPoto et al. | |
| 5,690,677 A | | 11/1997 | Schmieding et al. | |
| 5,697,950 A | | 12/1997 | Fucci et al. | |
| 5,707,395 A | | 1/1998 | Li | |
| 5,716,358 A | | 2/1998 | Ochoa et al. | |
| 5,720,766 A | | 2/1998 | Zang et al. | |
| 5,725,529 A | | 3/1998 | Nicholson et al. | |
| 5,728,116 A | | 3/1998 | Rosenman | |
| 5,730,744 A | | 3/1998 | Justin et al. | |
| 5,733,307 A | * | 3/1998 | Dinsdale | ................ 606/232 |
| 5,743,914 A | | 4/1998 | Skiba | |
| 5,797,963 A | | 8/1998 | McDevitt | |
| 5,814,071 A | | 9/1998 | McDevitt et al. | |
| 5,824,011 A | | 10/1998 | Stone et al. | |
| 5,827,291 A | | 10/1998 | Fucci et al. | |
| 5,851,219 A | | 12/1998 | Goble et al. | |
| 5,860,978 A | | 1/1999 | McDevitt et al. | |
| 5,868,747 A | | 2/1999 | Ochoa et al. | |
| 5,868,749 A | | 2/1999 | Reed | |
| 5,871,486 A | | 2/1999 | Huebner et al. | |
| 5,876,435 A | | 3/1999 | Swords et al. | |
| 5,895,396 A | | 4/1999 | Day et al. | |
| 5,895,425 A | | 4/1999 | Grafton et al. | |
| 5,904,696 A | | 5/1999 | Rosenman | |
| 5,904,704 A | | 5/1999 | Goble et al. | |
| 5,911,721 A | | 6/1999 | Nicholson et al. | |
| 5,931,840 A | | 8/1999 | Goble et al. | |
| 5,941,882 A | | 8/1999 | Jammet et al. | |
| 5,961,524 A | * | 10/1999 | Crombie | ................ 606/73 |
| 5,964,768 A | | 10/1999 | Huebner | |
| 5,964,783 A | | 10/1999 | Grafton et al. | |
| 5,967,783 A | | 10/1999 | Ura | |
| 5,968,044 A | | 10/1999 | Nicholson et al. | |
| 5,968,047 A | | 10/1999 | Reed | |

| | | |
|---|---|---|
| 5,976,134 A | 11/1999 | Huebner |
| 5,984,927 A | 11/1999 | Wenstrom, Jr. et al. |
| 6,027,523 A | 2/2000 | Schmieding |
| 6,036,701 A | 3/2000 | Rosenman |
| 6,045,573 A | 4/2000 | Wenstrom, Jr. et al. |
| 6,096,060 A | 8/2000 | Fitts et al. |
| 6,117,162 A | 9/2000 | Schmieding et al. |
| 6,139,565 A | 10/2000 | Stone et al. |
| 6,146,387 A | 11/2000 | Trott et al. |
| 6,214,031 B1 | 4/2001 | Schmieding et al. |
| 6,299,615 B1 | 10/2001 | Huebner |

FOREIGN PATENT DOCUMENTS

| | | |
|---|---|---|
| EP | 0409364 A2 | 1/1991 |
| EP | 0451932 A1 | 10/1991 |
| EP | 052059 A1 | 9/1992 |
| EP | 0528573 A1 | 2/1993 |
| EP | 057407 A1 | 12/1993 |
| EP | 0615732 A1 | 9/1994 |
| EP | 0674880 A1 | 10/1995 |
| EP | 0714643 | 5/1996 |
| FR | 2395738 | 1/1979 |
| FR | 2584151 A | 1/1987 |
| FR | 2 622 430 | 5/1989 |
| FR | 2788215 | 7/2000 |
| SU | 940375 A | 6/1980 |
| SU | 940376 A | 6/1980 |
| SU | 1097307 A | 2/1983 |
| WO | 86/03666 | 7/1966 |
| WO | 89/01767 | 3/1989 |
| WO | 89/09030 | 10/1989 |
| WO | 90/08510 | 8/1990 |
| WO | PCT/US 94/14071 | 12/1994 |
| WO | 95/15726 | 6/1995 |
| WO | PCT/US 98/00417 | 3/1998 |
| WO | WO 99/18873 | 4/1999 |

OTHER PUBLICATIONS

Anspach Anchor (undated).

M. Kurosaka Fixation Screw, DePuy Advertisement © 1987, 1988.

Kurosaka et al., "A Biomechanical Comparison of Different Surgical Techniques of Graft Fixation in Anterior Cruciate Ligament Reconstruction," American Journal of Sports Medicine, vol. 15, No. 3, pp. 225–229 (1987).

Lambert, K. L., "Vascularized Patellar Tendon Graft with Rigid Internal Fixation for Anterior Cruciate Ligament Insufficiency," Clinical Orthopedics and Related Research, No. 172 (Jan.–Feb. 1983).

Lambert et al., "Anatomic Substitution of the Ruptured ACL Using a Vascularized Patellar Tendon Graft with Interference Fit Fixation", The Crucial Ligaments, pp. 401–408.

Guhl, J.F., "Arthroscopic Management of Osteochondritis Dissecans," Techniques in Orthopedics, vol. 5, Chapter 6, pp. 63–84 (1995).

Nikolaou et al., "Anterior cruciate ligament allograft transplantation," American Journal of Sports Medicine, vol. 14, No. 5 (1986).

ROC™ Fastener System, Innovasive Devices, Inc. (1994).

* cited by examiner

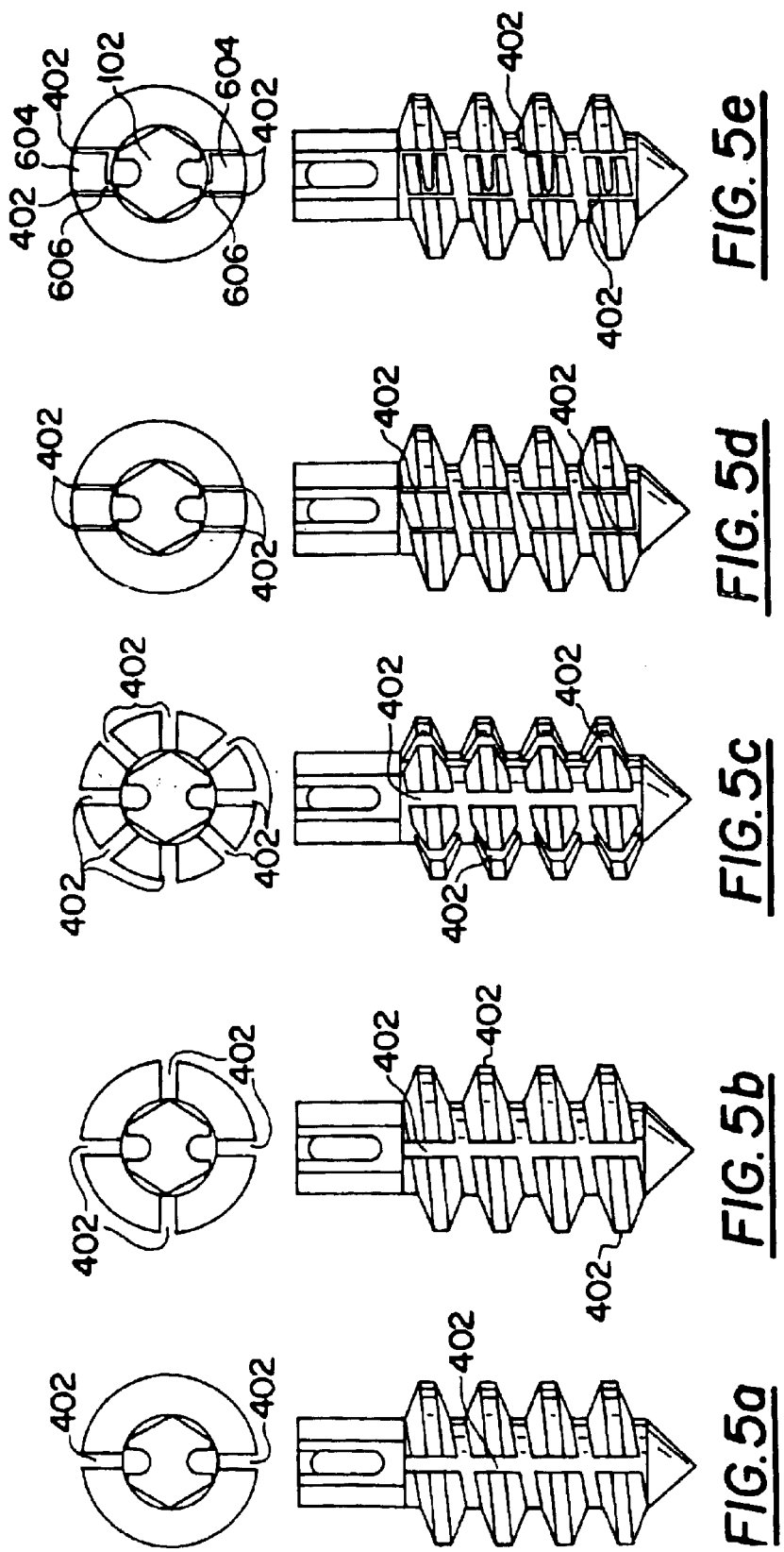

MEDICAL SCREW AND METHOD OF INSTALLATION

TECHNICAL FIELD

This invention generally relates to methods and apparatus for fastening fractured bones and for attaching soft tissue to bone tissue. More particularly, this invention relates to a surgical medical screw having a "Hi-Lo" thread configuration for increasing the pullout strength of the screw, a distal guiding tip for guiding the screw into a pre-drilled implantation site, and a counter-rotation device for resisting loosening of the screw from the implantation site.

BACKGROUND OF THE INVENTION

Medical screws are commonly used for a variety of surgical procedures. Medical screws may be used as suture anchors to attach a suture to a bone so that the suture may be used to hold soft tissue, such as torn tendons or ligaments, adjacent to the bone. Medical screws may also be used as fastening devices to attach prosthetics such as fixation plates to bone or to join portions of a fractured bone to aid the healing process. The multiple threads of such medical screws improve surgical repair by increasing the "pullout strength" of the screw, that is, the screw's ability to resist being pulled out from the bone. The threads also reduce the time and force required to implant the screw into the bone.

Various medical screws have been used for attaching objects, such as sutures, plates, or other bone fragments, to bone. U.S. Pat. No. 5,743,914 (Skiba) teaches a bone screw having a head for receiving a screw driving device, a shaft having a first series of helical threads having a first diameter and a first pitch, and second series of helical threads interleaved with said first series of helical threads and having a second diameter and a second pitch, wherein the second diameter is substantially different than the first diameter and at least one of said first and second pitches changes along the length of the shaft. This bone screw exhibits increased pullout strength and is particularly useful for joining bone fragments or for anchoring prosthetics to bone.

U.S. Pat. No. 5,087,201 (Mondani et al.) discloses a self-threading pin which is screw-threaded into the maxilla bone for implantation of a dental prosthetic. The pin has a screw-threaded shank portion, a driving head at one end of the shank portion and a drill bit at the other end of the shank portion. The screw-threaded shank portion of the pin has two intercalated screw threads of different heights.

All of the bone screws disclosed in the prior art generally utilize standard helical thread configurations. The above-described prior art further discloses thread configurations having two different helical threads of different heights interleaved with each other. However, often times these screws are difficult to insert in a pre-tapped/pre-drilled implantation site because there is no guiding mechanism which aids in aligning the screw with the implantation site. Further, the screws of the prior art are apt to counter-rotate, thereby becoming loose from the implantation site.

A medical screw is thus needed which overcomes the shortcomings of the prior art.

SUMMARY OF INVENTION

A medical screw device according to the present invention addresses many of the shortcomings of the prior art.

In accordance with one aspect of the present invention, a medical screw comprises a head for receiving a screw driving device and a shaft extending from the head. The shaft generally includes respective alternating first and second helical threads running substantially parallel with each other along the shaft (i.e., not intersecting). Additionally, in accordance with the present invention, the second series of helical threads advantageously exhibits a diameter different than the diameter of the first series of helical threads.

In accordance with an alternative embodiment of the present invention, the medical screw may comprise a plurality of series of helical threads, each exhibiting different diameters from the others. In accordance with this embodiment, the plurality of series of threads alternate and run substantially parallel with each other along the screw shaft.

In accordance with another aspect of the present invention, the medical screw may be configured with a variety of different head types and shapes.

In accordance with yet another aspect of the present invention, the medical screw may be manufactured from any type of bio-compatible material, for example, titanium alloy, stainless steel, class six implant grade plastic or a material made from bioabsobables such as polyglycolic acid and the like.

In accordance with yet another aspect of the present invention, the medical screw can exhibit any length, and the diameters of the shaft, the first series of threads and the second series of threads may differ for different types and sizes of the bone in which the screw is to be used.

In accordance with yet another aspect of the present invention, the medical screw comprises a distal guiding tip that aids in the insertion of the screw into a pre-tapped/pre-drilled implantation site in bone tissue.

In accordance with still another aspect of the present invention, the thickness of the first and/or second series of threads decreases along the shaft of the screw.

In accordance with yet another aspect of the present invention, the head of the medical screw comprises at least one eyelet for receiving a suture or multiple sutures.

In accordance with yet another aspect of the present invention, the medical screw comprises counter-rotation mechanisms for resisting loosening of the screw from the implantation site.

In accordance with still another aspect of the present invention, the Hi-Lo thread configuration may comprise a single, contiguous thread changing in height along the shaft of the screw.

These and other aspects of the present invention will become more apparent to those skilled in the art from the following non-limiting detailed description of preferred embodiments of the invention taken with reference to the accompanying figures.

BRIEF DESCRIPTION OF THE DRAWING FIGURES

Exemplary embodiments of the present invention will hereafter be described in conjunction with the appended drawing figures, wherein like designations denote like elements, and:

FIG. 4b is a top view of the exemplary embodiment of the medical screw of the present invention as shown in FIG. 4a;

FIGS. 5a–5e are side and top views of alternative embodiments of the medical screw of the present invention having counter-rotation channels;

DETAILED DESCRIPTION OF THE INVENTION

The following description is of exemplary embodiments only and is not intended to limit the scope, applicability or configuration of the invention in any way. Rather, the following description provides a convenient illustration for implementing exemplary embodiments of the invention. Various changes to the described embodiments may be made in the function and arrangement of the elements described without departing from the scope of the invention as set forth in the appended claims.

Figure 1:
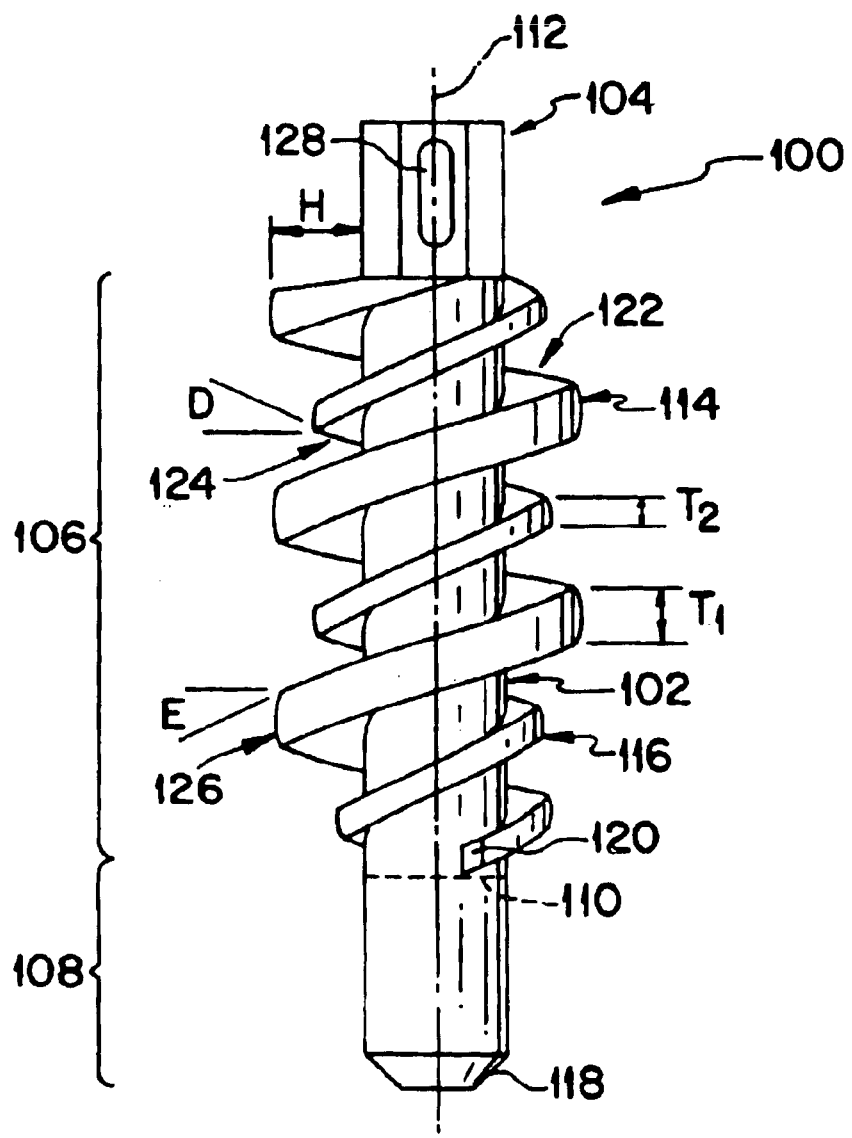
FIG. 1 is a side view of an exemplary embodiment of the medical screw of the present invention.

Referring now to FIG. 1, an exemplary embodiment of a medical screw 100 suitably comprises a shaft 102 and a head 104. Shaft 102 is suitably integral with head 104 and, in an exemplary embodiment, is substantially cylindrical in shape. However, in accordance with a further embodiment of the invention, shaft 102 may exhibit any suitable configuration. For example, referring momentarily to FIG. 7, shaft 102 may be tapered. That is, the diameter of the shaft may get larger toward the head of the screw. Shaft 102 may be configured to exhibit any length depending on the nature and type of bone it is intended to be used with or the purpose for which it is being used.

Referring again to FIG. 1, shaft 102 further comprises a thread portion 106 proximate to head 104 and a distal guiding tip 108. Thread portion 106 and distal guiding tip 108 are separated by an imaginary plane 110 perpendicular to a longitudinal axis 112 of shaft 102. In accordance with an exemplary embodiment of the present invention, thread portion 106 of shaft 102 may comprise two threads, major threads 114 and minor threads 116. In the illustrated embodiment, threads 114 and 116 are each suitably arranged in a helical pattern and run substantially parallel to one another, alternating along shaft 102 of screw 100. However in accordance with a further embodiment of the invention, thread portion 106 may comprise one, two, three or more threads, also of a helical pattern and interleaved in a suitable manner.

Distal guiding tip 108 of shaft 102 may be tapered to a point or, as in the illustrated embodiment, may terminate in a beveled tip 118 for pre-tapped applications that employ conventional pre-tapping methodologies (e.g. pre-drilling and the like). It should be appreciated, however, that self-tapping or self-drilling end configurations may be used; for example, tapping flutes or the like. As discussed more fully below, distal guiding tip 108 serves as a guiding or alignment device, aiding the surgeon in guiding and aligning screw 100 to a pre-tapped/pre-drilled implantation site.

Threads 114 and 116 are oriented in an alternating or interleaved thread pattern with different diameters in a so-called "Hi-Lo configuration." As will be appreciated, such a configuration includes minor threads having a height H measured from the surface of shaft 102 of between about 5% to about 99% and more preferably between about 25% to about 75%, and most preferably about 50% of the height of the major threads. Such a configuration with bone screws is believed to offer advantages over other bone screw configurations because it allows for greater recruitment of bone material, and particularly of the soft cancellous bone matter which is typically the part of the bony anatomy to which many screws fasten. Also, the Hi-Lo thread configuration of the preferred embodiment increases the shear strength near the outer edges of the major threads, thus further increasing the pullout strength of the screw. Finally, because only half of the threads have a large height, the amount of torque required to drive/set the screw tends to be reduced. While FIG. 1 shows two thread series 114, 116, it may appreciated that screw 100 may have one contiguous thread that changes in height along shaft 102.

With continuing reference to FIG. 1, threads 114 and 116 have equal and constant pitch along thread portion 106. As used herein, "pitch" is defined as the distance from the center of one thread to the center of the next thread. This applies no matter whether the screw has one, two, three or more series of threads. As may be appreciated, the pitch of at least one of the series of threads may vary along shaft 102. Because the pitches of the threads on multi-thread screws is less than a single thread screw, fewer revolutions are necessary to implant the screw. Consequently, the surgeon can insert the screw into bone faster, thereby reducing surgical time. The distal ends of threads 114 and 116 may taper in diameter toward shaft 102 as they approach imaginary plane 110 or, as illustrated, may terminate at plane 110 exposing a face 120.

Threads 114 and 116 also may be suitably finished to minimize stress on the bony material as screw 100 is inserted therein. In accordance with an exemplary embodiment of this aspect of the present invention, the outer surfaces or edges of threads 114, 116 are optimally rounded or smoothed. As will be appreciated, such finish can be engendered through electro-polishing, fine bead sanding or the like.

With continued references to FIG. 1, in accordance with the illustrated embodiment of the invention, each of respective threads 114 and 116 preferably comprise an angled helical upper surface 122, an angled helical under surface 124 and a helical edge 126 interconnecting surfaces 122 and 124. The thickness $T_1$ of helical edge 126 of major thread 114 is greater than the thickness $T_2$ of helical edge of minor thread 116. Threads of different thicknesses prevent "cross-threading" of the screw as it is rotated into a pre-drilled implantation site. The term "cross-threading" refers to an objectionable state where a first thread of the screw has begun to advance into a pre-drilled thread track in the implantation site that does not correspond to the first thread. Cross-threading requires higher insertion torques to drive the screw because the larger diameter threads must displace bone as the screw advances. If the screw is made of a polymer, it may not have the shear strength to withstand such stresses. If the different thread series are different in thicknesses, cross-threading cannot occur.

Preferably, surface 124 is downwardly angled from the outer edge of threads 114 and 116 to the body of shaft 102. This angle is illustrated by dimension D. Similarly, upper surface 122 is preferably angled upwardly from the helical edge 126 of threads 114, 116 to the body of shaft 102, as is illustrated by dimension E. It should be noted that the angles of the upper and lower surfaces of the major threads 114 may differ from those of minor threads 116 depending on the particular thread configuration. Further, the angles of the upper and lower surfaces of at least one of the threads 114, 116 may also vary along shaft 102. Similarly, the thicknesses $T_1$, and/or $T_2$ may increase or decrease along shaft 102, as discussed in more detail below with reference to FIG. 8.

Referring again to FIG. 1, head 104 at the proximate end of screw 100 is designed to fit the head of a driver device. Head 104 may be of a square, rectangular or hexagonal shape or, alternatively, may be of any shape suitable to engage a driver for rotation of screw 100.

In further embodiments, head 104 may include an eyelet 128 of sufficient size to receive one or more sutures. Eyelet 128 may be of any suitable size to accept any suture material or may come in a range of sizes specific to different suture types. In alternative embodiments, head 104 may include a plurality of eyelets to enable one or more sutures to pass through two or more such eyelets.

In accordance with a further aspect of the present invention, screw 100 may be advantageously made from any suitable bio-compatible material, for example, titanium alloy, stainless steel, class six implant grade plastic, and the like, or any other bio-compatible material which exhibits adequate pullout strength and has sufficiently low brittleness to avoid breakage during long term usage of the device in suture. Alternatively, if screw 100 will be used for an application that does not require a relatively long useful life of the screw, screw 100 may be made from a suitable bio-absorbable material, for example, polylactic, polyoxalic or polyglycolic acids or the like.

Figure 2A:
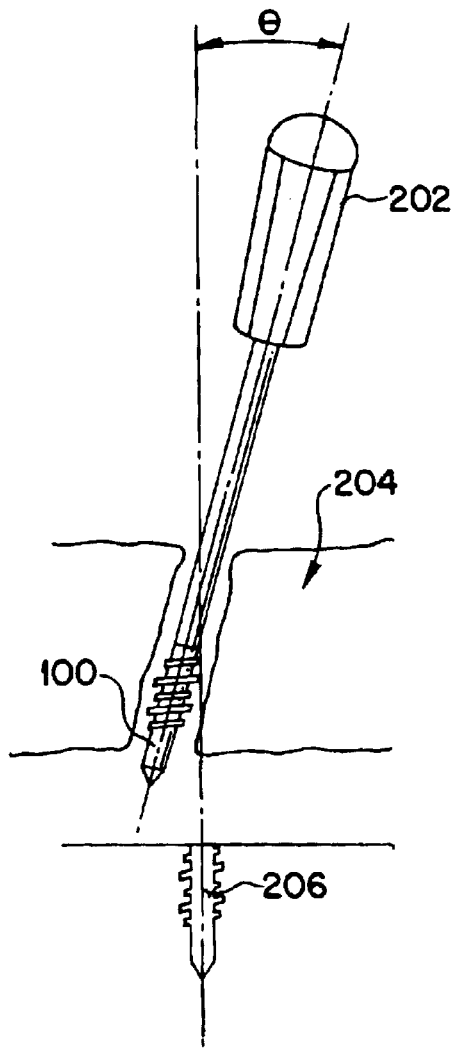
FIG. 2a is a schematic view of an exemplary embodiment of the medical screw of the present invention connected to a driver and inserted into tissue.
Figure 2B:
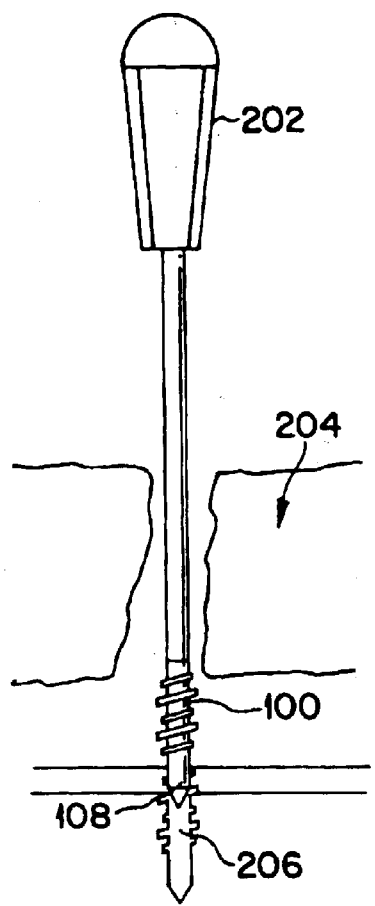
FIG. 2b is a schematic view of an exemplary embodiment of the medical screw of the present invention connected to a driver and aligned with a pre-drilled implantation site.

As noted above, distal guiding tip 108 serves as a guiding or alignment device that aids a surgeon in guiding and aligning screw 100 to a pre-tapped/pre-drilled implantation site. The portal of entry of screw 100 may not be perfectly aligned with the implantation site. As shown in FIG. 2a, it may be difficult for the surgeon to align screw 100 to the implantation site as screw 100 often must pass through multiple layers of soft tissue 204. Thus, screw 100 and a driver 202, in combination, may approach the implantation site 206 at an angle θ (theta) rather than approaching the site in alignment with the longitudinal axis of the site. FIG. 2b shows screw 100, in combination with driver 202, in alignment with implantation site 206. The surgeon typically will use the driver device 202 and screw 100 in combination to move the tissue 204 and guide screw 100 into the pre-drilled implantation site 206. By using distal guiding tip 108, the surgeon is able to locate the opening of implantation site 206 and insert distal guiding tip 108 into implantation site 206. The surgeon may then exert a moment on screw 100 and driver device 202, using the outside diameter surface of distal guiding tip 108 and the inside diameter of the core of implantation site 206 as bearing surfaces, thereby reducing movement of screw 100 and flexion of screw 100 as it enters implantation site 206 so that screw 100 can advance into the site with little resistance.

Figure 3:
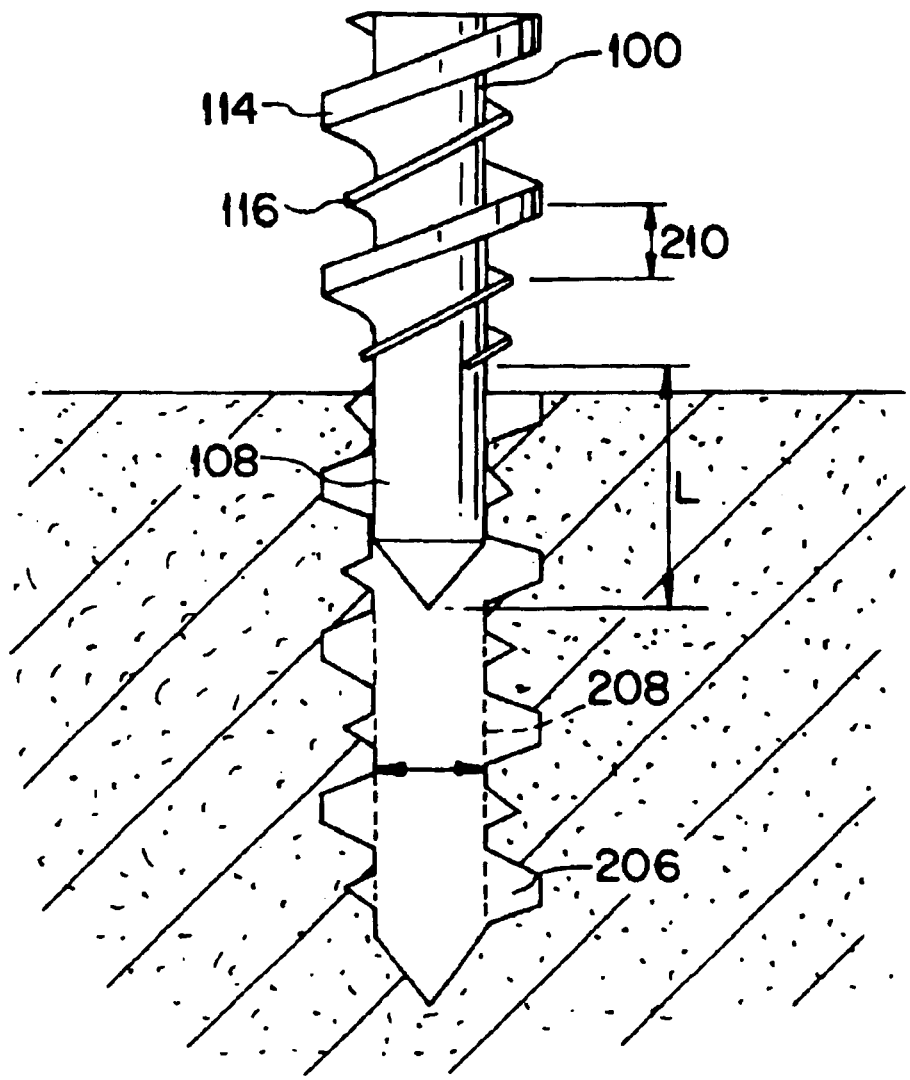
FIG. 3 is a schematic view of an exemplary embodiment of the medical screw of the present invention showing the distal guiding tip inserted into a pre-drilled implantation site.

FIG. 3 shows in further detail implantation of screw 100 into implantation site 206. Implantation site has been pre-tapped/pre-drilled with tracks that correspond to the threads 114, 116 of screw 100. In one embodiment of the invention, all features of implantation site 206 are appropriately 90% of the size of screw 100, except for the core 208 of implantation site 206. The diameter of core 208 may be equal to the diameter of shaft 102 of screw 100. The advantage of this feature is that, as the screw is driven into the bone, the screw threads displace bone, increasing the localized bone density (known in the art as "radial osteo-compression") without over stressing screw 100 upon implantation. In other alternative embodiments, the dimension of implantation site 206 may be equal to, smaller than or slightly larger than the dimensions of screw 100.

With continued reference to FIG. 3, the length L of distal guiding tip 108 may be equal to or greater than the distance 210 between thread centers, although it is desirable that distal guiding tip 108 not be so long as to require a corresponding implantation site that sacrifices an unnecessary amount of bone. With length L of distal guiding tip 108 equal to at least the distance between two adjacent thread centers, the distal guiding tip 108 contacts three or more points located in an imaginary cylindrical plane of core 208, thereby constraining screw 100 from lateral or side-to-side movement.

As shown in FIG. 3, distal guiding tip 108 terminates at a pointed tip. The taper of the pointed tip may be 90° or less as measured from an axis parallel to the longitudinal axis of shaft 102. Alternatively, distal guiding tip 108 may terminate in a beveled tip, as shown in FIG. 1.

Figure 4A:
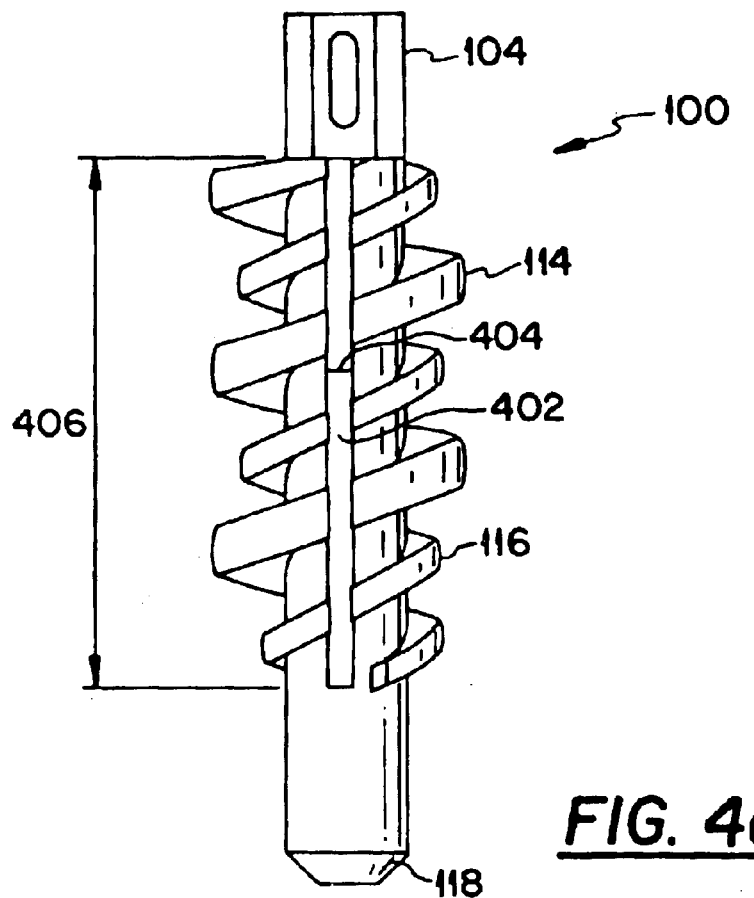
FIG. 4a is a side view of another exemplary embodiment of the medical screw of the present invention having a counter-rotation channel.
Figure 4B:
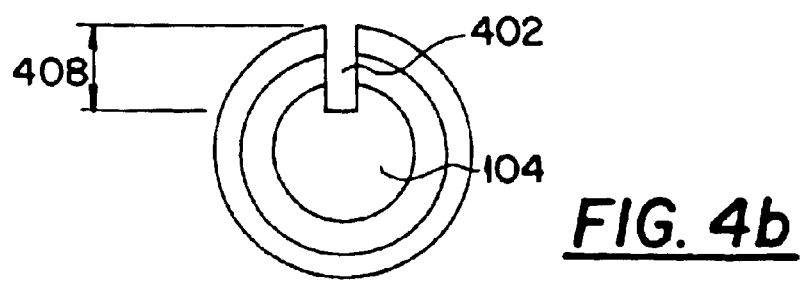

FIGS. 4a and 4b show an alternative embodiment of the invention having a counter-rotation channel 402. Counter-rotation channel 402 has a length 406, and a width 404. Counter-rotation channel also has a depth 408 that intersects threads 114, 116 and may also intersect a portion of shaft 102. As bone heals, trabeculae grows into counter-rotation channel 402 increasing the torque required to unscrew screw 100 from the bone, thereby reducing the likelihood that screw 100 will loosen from the implantation site. While FIGS. 4a and 4b show screw 100 with one counter-rotation channel 402, it will be appreciated that screw 100 may have more than one counter-rotation channel to further reduce the likelihood that screw 100 will loosen from the implantation site. As shown in FIGS. 5a–5e, screw 100 may have two or more counter-rotation channels 402. However, if more than one counter-rotation channel is employed, it is preferable that the multiple channels be spaced equally apart around shaft 102 so as to maintain the balance of screw 100 as it is rotated into an implantation site.

Figure 11A:
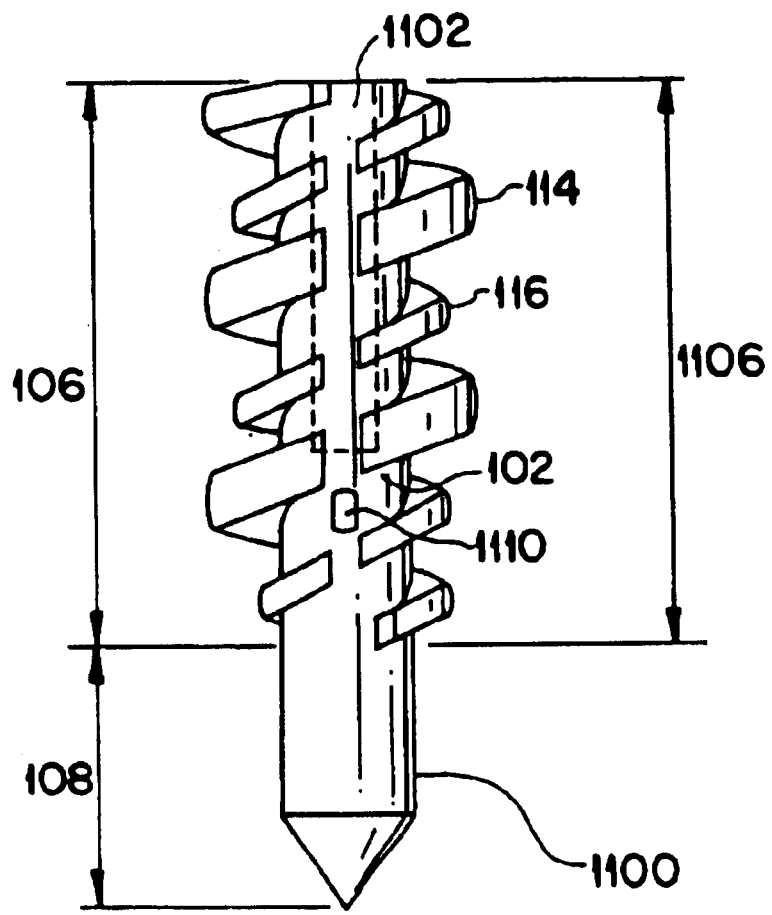
FIGS. 11a and 11b are side and top views, respectively, of alternative embodiments of the medical screw of the present invention.
Figure 11B:
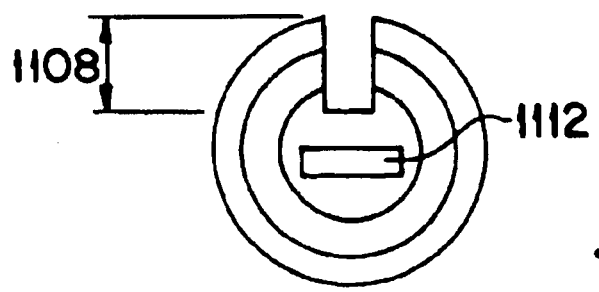

Referring momentarily to FIGS. 11a and 11b, an alternative embodiment of the invention, screw 1100, is shown having at least one counter-rotation channel 1102. Counter-rotation channel 1102 has a length 1106 and a depth 1108 that intersects threads 114, 116 and may also intersect a portion of shaft 102. Screw 1100 further has a slot 1112 for receiving internally a driving device for advancing and securing screw 1100 into a pre-drilled/pre-tapped implantation site. Screw 1100 may also have at least one eyelet 1110 for receiving sutures. Eyelet 1110 extends through shaft 102 perpendicular to the longitudinal axis of shaft 102 and the longitudinal axis of the counter-rotation channel. Eyelet 1110 is positioned below slot 1112 and may be positioned within threaded portion 106 or along the distal guiding tip 108.

Figure 6C:
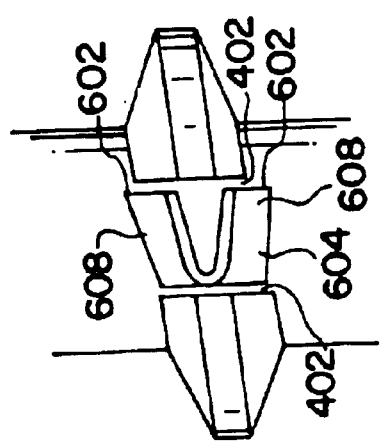
FIGS. 6a–6c are side views of counter-rotation teeth of the present invention.
Figure 6B:
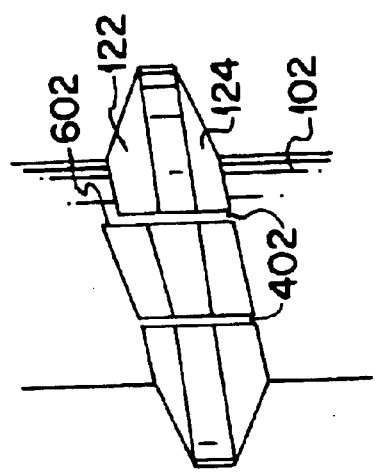
Figure 6A:
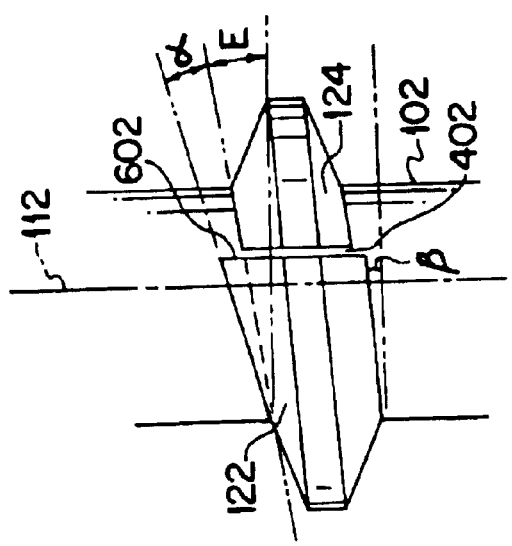

Referring to FIG. 6a–6c, screw 100 may have counter-rotation elements in addition to counter-rotation channels 402. In FIG. 6a, at least one of threads 114, 116 may have at least one edge or "tooth" 602. Tooth 602 is integral with the thread but rises adjacent counter-rotation channel 402 at an angle α (alpha) beyond angle E of upper surface 122. Angle α is preferably in a range of about 1 degree to 45 degrees. Alternatively, tooth 602 may be integral with under surface 124 and may extend an angle β (beta) above an axis perpendicular to the longitudinal axis 112 of shaft 102. As screw 100 is rotated into place, the surrounding bone compresses and deforms around the threads. Once screw 100 is in place, the bone decompresses and surrounds screw 100. Tooth 602 will prevent counter-rotation of screw 100 by effecting resistance against the bone of the implantation site which surrounds screw 100. In an alternative embodiment, as shown in FIGS. 5d and 6b, screw 100 may have multiple counter-rotation channels 402 and one or more teeth 602.

Referring to FIGS. 5e and 6c, a further embodiment of the present invention includes spring-loaded thread members 604 with teeth 602. As shown in FIG. 5e, spring-loaded thread members 604 are connected to shaft 102 by connector members 606. Spring-loaded thread members 604 have two fingers 608 that are integrally connected at one end, which end is connected to shaft 102 by connector member 606, and that terminate at their respective ends at teeth 602. When screw 100 is rotated into the implantation site, fingers 608 are forced slightly together by bone. During healing, bone grows into counter-rotation channel 402 and into the space between fingers 608. When torque is applied to screw 100 in a counter-rotation direction, the bone between fingers 608 spreads fingers 608 apart, thereby exposing teeth 602 which resist counter-rotation.

Figure 7:
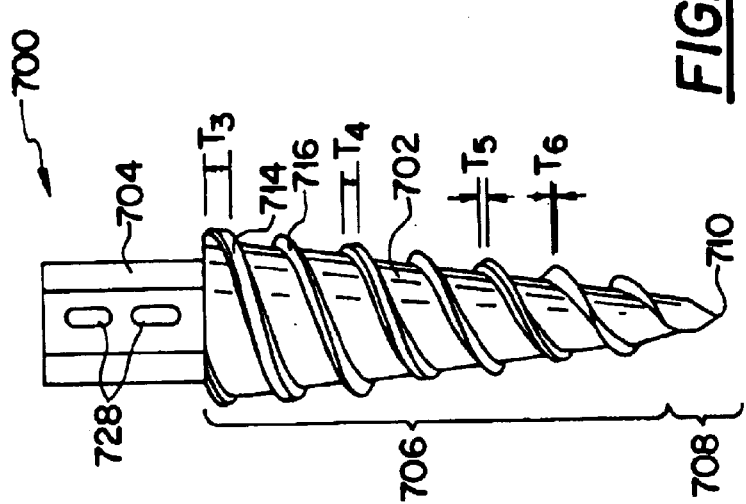
FIG. 7 is a side view of another exemplary embodiment of the medical screw of the present invention.

FIG. 7 shows an alternative embodiment of the invention, a screw 700. In this embodiment, screw 700 has a tapered shaft 702 from a head 704 to the distal end of a distal guiding tip 708, terminating in a pointed tip 710. A threaded portion 706 of screw 700 has major threads 714 and minor threads 716. Major threads 714 decrease in thickness along shaft 702, from a thickness $T_3$ proximate to head 704 to a thickness $T_6$ proximate distal guiding tip 708. While only thread 714 is shown to decrease in thickness, it will be appreciated that thread 716 could likewise decrease in thickness along shaft 702. Head 704 has two eyelets 728 for receiving sutures. Alternatively, head 704 may have one, three or more eyelets for receiving sutures.

Figure 8:
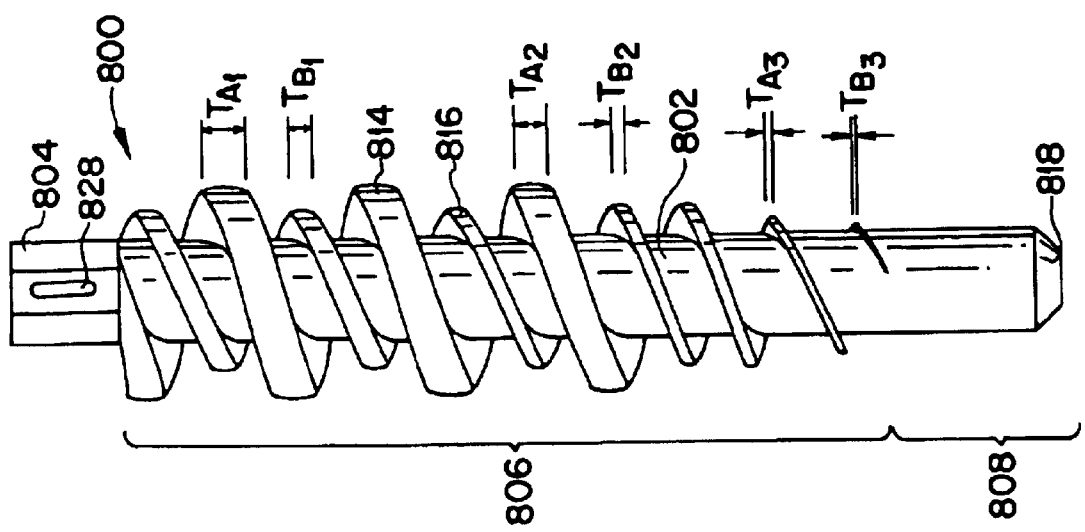
FIG. 8 is a side view of yet another exemplary embodiment of the medical screw of the present invention.

In a further alternative embodiment, referring to FIG. 8, a screw 800 may have a shaft 802 which is predominantly cylindrical in shape and terminates in a beveled tip 818. A threaded portion 806 of screw 800 has major threads 814 and minor threads 816. Threads 814, 816 both decrease in thickness from proximate a head 804 to proximate a distal guiding tip 808. While only two threads, threads 814, 816, are shown, it will be appreciated that screw 800 may have one, three, four or more threads. Head 804 has one eyelet 828, although head 804 may have any number of eyelets.

Figure 9:
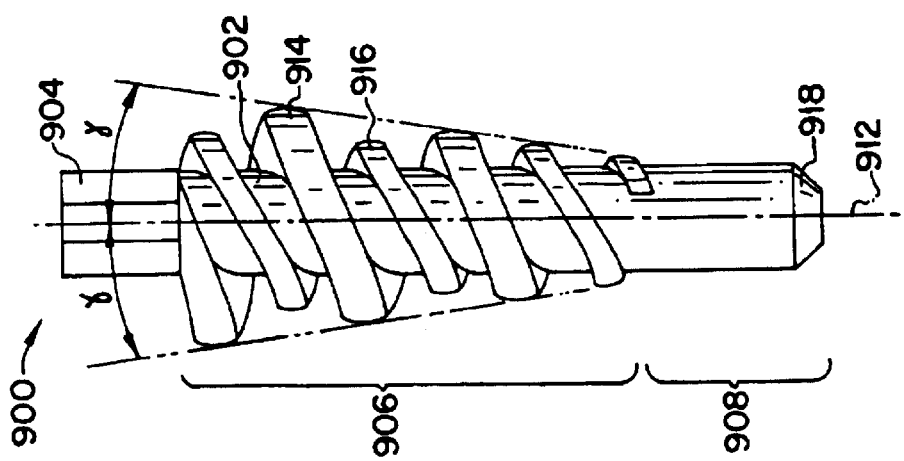
FIG. 9 is a side view of still yet another exemplary embodiment of the medical screw of the present invention.

In another embodiment of the present invention, as shown in FIG. 9, a screw 900 may have a shaft 902 which is predominantly cylindrical and terminates in a beveled tip 918. Alternatively, shaft 902 may terminate in a tapered tip. A threaded portion 906 of screw 900 has major threads 914 and minor threads 916. Threads 914, 916 taper in diameter from a larger diameter proximate to a head 904 to a smaller diameter proximate to a distal guiding tip 908. Threads 914, 916 taper by an angle γ (gamma) measured from a longitudinal axis 912 of shaft 902, increasing radial osteocompression and thus increasing resistance to pull-out of screw 900. While shaft 902 is shown as cylindrical in shape, it will be appreciated that shaft 902 could taper from proximate head 904, to the distal end of threaded portion 906. Alternatively, shaft 902 may taper continuously from proximate head 904 terminating in a pointed tip at the distal end of a distal guiding tip 908. Further, although threads 914, 916 are shown with constant thickness along shaft 902, either thread 914 or 916 or both may decrease in thickness along shaft 902 from head 904 to proximate distal guiding tip 908.

Figure 10:
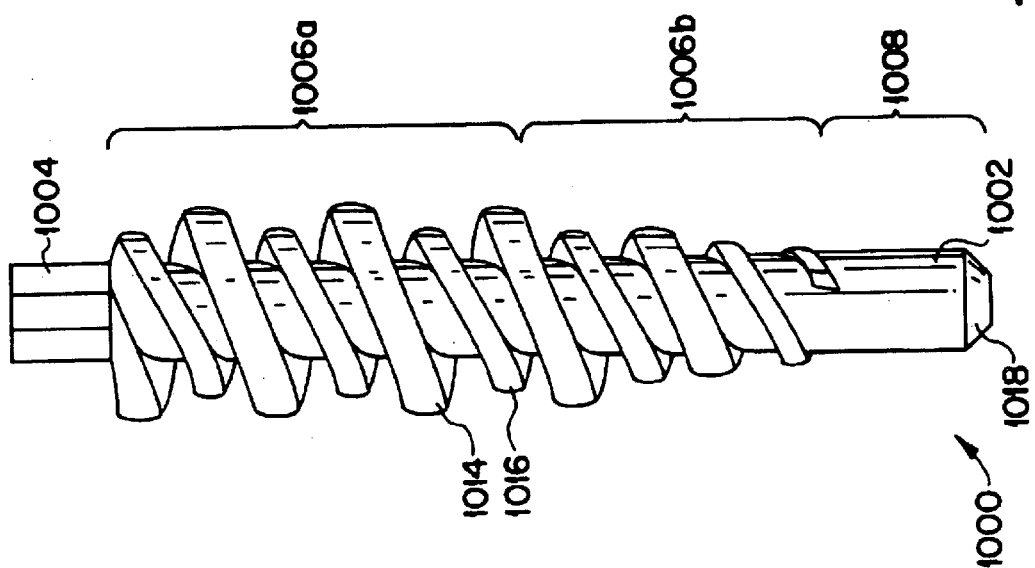
FIG. 10 is a side view of another exemplary embodiment of the medical screw of the present invention.

Referring now to FIG. 10, another embodiment of the present invention, a screw 1000, has a shaft 1002 which is predominantly cylindrical in shape and terminates in a beveled tip 1018. Screw 1000 comprises a first threaded portion 1006a and a second threaded portion 1006b. Major threads 1014 and minor threads 1016 extend from proximate a head 1004 through threaded portions 1006a, 1006b and terminate proximate to distal guiding tip 1008. Threads 1014, 1016 have constant diameters in first threaded portion 1006a but taper continuously from proximate first threaded portion 1006a through second threaded portion 1006b. While shaft 1002 is shown as predominantly cylindrical, it will be appreciated that shaft 1002 may taper continuously from the distal end of first threaded portion 1006a through second threaded portion 1006b. Alternatively, shaft 1002 may taper from the distal end of first threaded portion 1006a through second threaded portion 1006b and distal guiding tip 1018, terminating in a pointed tip. In a further embodiment, shaft 1002 may taper from head 1004 along the entire length of shaft 1002, terminating in a pointed tip. Similarly, it will be appreciated that, while threads 1014, 1016 are shown with constant thickness, threads 1014, 1016 may decrease in thickness in first threaded portion 1006a and/or second threaded portion 1006b.

Although the subject invention has been described herein in conjunction with the appended drawing Figures, it will be appreciated that the scope of the invention is not so limited. Various modifications in the arrangement of the components discussed and the steps described herein for using the subject device may be made without departing from the spirit and scope of the invention as set forth in the appended claims.

We claim:

1. A method of installing a medical screw comprising the steps of:

providing a medical screw having a head for receiving a screw driving device and a shaft extending from said head along a longitudinal axis, wherein said shaft includes (a) a threaded portion including helical threads and (b) a distal guiding tip extending longitudinally and distally from the threaded portion and including a cylindrical portion;

drilling an implantation site into bone at a desired location, the implantation site having a cylindrical core;

tapping the cylindrical core with tracks that correspond to the helical threads; and inserting said distal guiding tip into said implantation site at a depth sufficient that a surface of the cylindrical portion contacts at least three points on the cylindrical core with each of the at least three points being separated by a track.

2. The method of claim 1 further comprising rotating said medical screw to a desired degree of installation.

3. The method of claim 2 wherein rotating said medical screw comprises inserting a screw driving device into a slot formed on said head and rotating said screw driving device.

4. The method of claim 1 wherein inserting said distal guiding tip comprises inserting a screw driving device into a slot formed on said head.

* * * * *